United States Patent

Kanai et al.

[11] Patent Number: 6,118,522
[45] Date of Patent: Sep. 12, 2000

[54] APPARATUS AND METHOD FOR DIFFERENTIATING ERYTHROCYTES IN URINE

[75] Inventors: Kazuyuki Kanai, Kasai; Masakazu Fukuda, Kobe, both of Japan

[73] Assignee: Sysmex Corporation, Hyogo, Japan

[21] Appl. No.: 09/288,503

[22] Filed: Apr. 8, 1999

[30] Foreign Application Priority Data

Apr. 8, 1998 [JP] Japan ................... 10-135887

[51] Int. Cl.$^7$ .................................. G01N 15/02
[52] U.S. Cl. .................. 356/73; 356/336; 356/338; 356/39; 436/63; 435/39
[58] Field of Search ................ 356/73, 318, 336, 356/337, 338, 339, 340, 341, 342; 364/413.01, 413.11; 435/39, 7.24, 7.25, 29, 38; 436/63, 52, 66, 8, 10, 16, 17, 18, 172

[56] References Cited

U.S. PATENT DOCUMENTS

| 5,325,168 | 6/1994 | Nakamoto et al. ........... 356/336 |
| 5,408,307 | 4/1995 | Yamamoto et al. ........... 356/73 |
| 5,731,867 | 3/1998 | Katayama ................... 356/338 |
| 5,891,733 | 4/1999 | Inoue ...................... 436/63 |
| 5,917,584 | 6/1999 | Li et al. .................. 356/73 |

FOREIGN PATENT DOCUMENTS

8240520   9/1996   Japan.

*Primary Examiner*—Hoa Q. Pham

[57] ABSTRACT

An apparatus for differentiating erythrocytes in urine includes: a sheath flow cell for forming a urine specimen flow by surrounding a urine specimen with a sheath liquid, the urine specimen containing particles; a light application device for applying light to the urine specimen flow; a light detector for detecting a light signal emitted by each particle in the urine specimen flow; an identification device for identifying erythrocytes from the particles in the urine specimen flow in accordance with the detected light signal; a particle size distribution preparing device for preparing a particle size distribution diagram of the identified erythrocytes; a determining device for determining an origin of the erythrocytes in accordance with an erythrocyte size value at which an accumulated frequency of erythrocytes as counted from a smallest size in the particle size distribution diagram agrees with a preset value larger than half of a total accumulated frequency in the particle size distribution diagram; and an output device for outputting a determination result.

29 Claims, 7 Drawing Sheets

APPARATUS AND METHOD FOR DIFFERENTIATING ERYTHROCYTES IN URINE

CROSS-REFERENCES TO RELATED APPLICATIONS

This application is related to and claims 35 USC §119 priority of Japanese patent application No. HEI 10-135887 filed on Apr. 8, 1998, the disclosure of which is incorporated herein by reference in its entirety.

BACKGROUND OF THE INVENTION

1. Field of the Invention

The present invention relates to an apparatus and method for differentiating erythrocytes in urine, and more particularly to an apparatus and method using flow cytometry for differentiating erythrocytes in urine to determine the origin and type of the erythrocytes.

2. Description of the Related Art

There are two cases that give rise to hematuria, where erythrocytes appear in urine. Hematuria of glomerular origin is caused by an internal disease such as nephritis, whereas hematuria of non-glomerular origin occurs by a urinary disease such as bladder cancer, kidney cancer, and urethral calculi. When hematuria is observed, it is necessary to search for the cause thereof.

Methods conventionally known for determining whether erythrocytes in urine are of glomerular origin (an internal disease) or non-glomerular origin (a urinary disease) are:

(a) using a microscope to differentiate erythrocytes in accordance with their morphological differences, and (b) using an automatic blood cell counting apparatus to differentiate erythrocytes in accordance with the differences in their size.

However, according to method (a), there is a problem that inspection for morphological differences is complicated and takes a lot of time. Also, it is difficult to maintain reliability of the inspection because it is based on human eye inspection which requires expertise.

According to method (b), there is a problem that a pretreatment such as centrifugal separation is required because it is necessary to make measurements with the electric conductivity of a urine specimen maintained at a constant value. Also, there is a fear that the accuracy of judgment decreases by mistakenly identifying what is not an erythrocyte (for example, a bacterium or a crystalline component) as an erythrocyte.

In order to solve the above-mentioned problem, there is known (c) a new apparatus which differentiates erythrocytes, leukocytes, epithelial cells, urinary casts, and bacteria by processing the optical signal intensities of scattered light and fluorescent light of the particles as obtained from a flow cytometer, and analyzing erythrocytes in urine in accordance with a bias state of a particle size distribution of the differentiated erythrocytes (See Japanese Unexamined Patent Publication No. Hei 8(1996)-240520).

This apparatus recognizes that the erythrocytes of glomerular origin generally have smaller particle sizes than those of non-glomerular origin, whereby the group of erythrocytes whose particle size distribution is biased to a smaller size is classified as glomerular-origin erythrocytes, and the group of erythrocytes whose particle size distribution is biased to a larger size is classified as non-glomerular-origin erythrocytes.

Specifically, a calculating section of the apparatus calculates a number Raz of erythrocytes falling within a range from La to Lz, a number Ra2 of erythrocytes falling within a range from La to L2, and a number R1z of erythrocytes falling within a range from L1 to Lz, provided that La represents a lower limit of particle sizes in the erythrocyte size distribution, Lz represents an upper limit thereof, and L1 and L2 represent preset values satisfying the relation La<L1<L2<Lz.

A determining section of the apparatus determines the erythrocytes to be of glomerular origin when Ra2/Raz is greater than a first predetermined value and determines the erythrocytes to be of non-glomerular origin when R1z/Raz is greater than a second predetermined value. If neither of the above inequality relationships are satisfied, the erythrocytes are determined to be of mixed kind. If both of the above inequality relationships are satisfied, the erythrocytes are determined to be of non-glomerular origin.

The judgment in the prior art method (c) has been devised by considering that, although the particle size distribution of erythrocytes of non-glomerular origin has a peak biased to a larger size and the particle size distribution of erythrocytes of glomerular origin has a peak biased to a smaller size, there is an overlapping region (region where the two particle size distributions overlap with each other). In other words, the erythrocytes of non-glomerular origin are captured by using the ratio of erythrocytes having a particle size larger than a preset value including the overlapping portion, and the erythrocytes of glomerular origin are captured by using the ratio of erythrocytes having a particle size smaller than a preset value including the overlapping portion, so as to determine the origin of the erythrocytes.

However, the judgment actually carried out in an inspection room often did not coincide with the observation result obtained by microscopy.

This may have been brought about by the following reason. In this judgment, the erythrocytes that have a small size are determined as erythrocytes of glomerular origin, assuming that the erythrocytes of non-glomerular origin have a morphology similar to those in blood. However, the erythrocytes may be damaged in urine to give a signal that indicates a smaller size. The term "damage" as used herein refers to a damage of erythrocytes occurring in aciduria, hyposthenuria, or the like while the erythrocytes are in a bladder or in a urine specimen after urination.

Here, the term "glomerular origin" refers to urine containing a large proportion of deformed erythrocytes. The deformed erythrocytes are red blood cells that are deformed to have a characteristic shape by passing through a glomerulus of a kidney, and have a morphology different from that of damaged erythrocytes appearing in aciduria, hyposthenuria, or the like. In other words, the erythrocytes can be differentiated by the prior art method only under a condition in which the erythrocytes have not been damaged in urine.

SUMMARY OF THE INVENTION

The present invention has been made in view of these circumstances and the purpose thereof is to provide an apparatus and method for accurately determining the origin and type of erythrocytes in urine even if the urine suffers from aciduria, hyposthenuria, or the like.

Accordingly, the present invention provides an apparatus for differentiating erythrocytes in urine, including: a sheath flow cell for forming a urine specimen flow by surrounding a urine specimen with a sheath liquid, the urine specimen containing particles; a light application unit for applying light to the urine specimen flow; a light detector for detecting a light signal emitted by each particle in the urine specimen flow; an identification unit for identifying erythrocytes from the particles in the urine specimen flow in accordance with the detected light signal; a particle size distribution preparing unit for preparing a particle size distribution diagram of the identified erythrocytes; a determining unit for determining an origin of the erythrocytes in accordance with an erythrocyte size value at which an accumulated frequency of erythrocytes as counted from a smallest size in the particle size distribution diagram agrees with a preset value larger than half of a total accumulated frequency in the particle size distribution diagram; and an output for outputting a determination result.

Also, the present invention provides a method for differentiating erythrocytes in urine, including the steps of: forming a urine specimen flow by surrounding a urine specimen with a sheath liquid in a sheath flow cell, the urine specimen containing particles; applying light to the urine specimen flow using by light application unit; detecting a light signal emitted by each particle in the urine specimen flow using a light detector; identifying erythrocytes from the particles in the urine specimen flow in accordance with the detected light signal using an identification unit; preparing a particle size distribution diagram of the identified erythrocytes using a particle size distribution preparing unit; and determining an origin of the erythrocytes in accordance with an erythrocyte size value at which an accumulated frequency of erythrocytes as counted from a smallest size in the particle size distribution diagram agrees with a preset value larger than half of a total accumulated frequency in the particle size distribution diagram.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

The urine specimen in the present invention may be a specimen such as obtained by staining, with a fluorescent dye, an original urine or a urine diluted by a diluent.

The sheath flow cell for forming a urine specimen flow may be a flow cell capable of forming a narrow specimen flow by a hydrodynamical effect by surrounding a urine specimen containing particles, with a sheath liquid for flowing. For this purpose, conventionally known sheath flow cells may be used.

The light application means for applying a light to a urine specimen flow may be a means for continuously irradiating the urine specimen flow with a light. For this purpose, a light source such as a laser, a halogen lamp, or a tungsten lamp may be used.

Particles in a urine specimen flow may be solid components contained in urine, namely, erythrocytes, leukocytes, epithelial cells, bacteria, yeast-like fungi, sperms, and the like.

As the light detection means for detecting the intensity of light emitted by a particle, a photodiode or a phototransistor, for example, may be used for detecting an intensity of scattered light, and a photomultiplier tube may be used for detecting an intensity of fluorescent light.

The identification means for identifying erythrocytes from the particles in a urine specimen flow may be, for example, a means for making a two-dimensional scattergram (distribution diagram) by using, as parameters, intensities of the scattered light and the fluorescent light detected from each of the particles and for determining the particles falling within a preset distribution region as erythrocytes.

Figure 3:
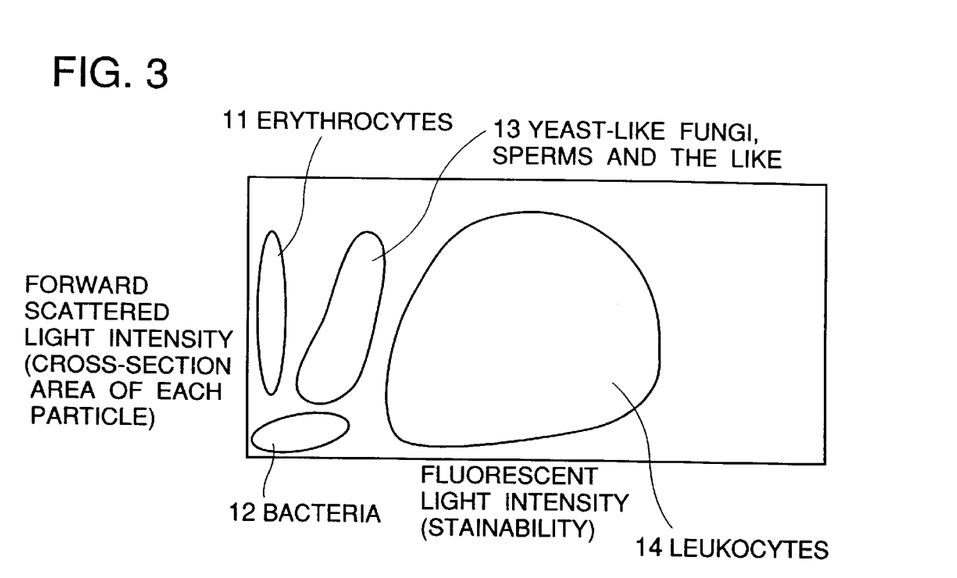
FIG. 3 is a view showing an example of a scattergram of "fluorescent light-scattered light" intensities obtained by the apparatus of the embodiment of the present invention.

In other words, since it is known in the art that the particles in a urine specimen have characteristics in their scattered light and fluorescent light intensities as shown in Table 1 and FIG. 3, those falling in the region on a scattergram with the scattered light intensity in the range from 40 to 140 ch and with the fluorescent light intensity in the range from 20 to 30 ch may be identified as erythrocytes. Here, the unit "ch" represents a relative frequency of the scattered light intensity, and 100 ch as converted into an erythrocyte size corresponds to about 5 μm. Methods for identifying the erythrocytes are not limited to the above-mentioned approach.

TABLE 1

| Particles | Scattered light intensity | Fluorescent light intensity |
|---|---|---|
| Erythrocytes | 40–140 | 20–30 |
| Leukocytes | 80–200 | 100–200 |
| Epithelial cells | 300 or more | 300 or more |
| Bacteria | 80–100 | 50–80 |
| Yeast-like fungi | 80–140 | 50–100 |
| Sperms | 80–100 | 50–100 |

(units: ch)

The particle size distribution preparing means for preparing a particle size distribution diagram of erythrocytes based on the light signal intensities of the identified erythrocytes may be a means for preparing a histogram of particle size distribution with the scattered light intensity used as a parameter because a scattered light intensity, especially a forward scattered light intensity, generally corresponds to cross-sectional area (particle diameter) of the particle. Here, side scattered light may be used instead of the forward scattered light although the side scattered light is liable to be affected by the shape or the surface condition of the erythrocytes.

The determining means for determining an origin of erythrocytes in accordance with an erythrocyte size value at which an accumulated frequency of erythrocytes as counted from a smallest size in the particle size distribution diagram agrees with a preset value larger than half of a total accumulated frequency in the particle size distribution diagram may be a means for determining whether the erythrocytes in the urine are of glomerular origin or non-glomerular origin in accordance with an erythrocyte size value at a preset position larger than the median of the erythrocyte size distribution diagram.

This judgment is based on the idea that some of the erythrocytes retain their original shape or a shape near to their original shape. This is due to the fact that, since damage of the erythrocytes in urine occurs while the urine is in a bladder or the like, the conditions under which damage occurs depends on the erythrocytes, and also the resistance of the membrane varies from erythrocyte to erythrocyte. In other words, the determining means monitors whether the erythrocytes retaining their original shape remain in the urine specimen or not by inspecting an erythrocyte size value at a preset position larger than the median of the erythrocyte size distribution diagram.

Thus, if this erythrocyte size value is larger than a preset standard, the determining means determines that the erythrocytes are of non-glomerular origin, because some of the erythrocytes retain their original shape. On the other hand, if this erythrocyte size value is smaller than the preset standard, the determining means determines that the erythrocytes are of glomerular origin, because no erythrocytes retain their original shape.

Also, two preset standards for the erythrocyte size may be used to determine that the erythrocytes falling between the two preset standards are of mixed kind which cannot be classified into any of the above-mentioned two kinds (non-glomerular and glomerular).

Specifically, a preset value A % ($50 < A \leq 100$) may be used to calculate a position at which the accumulated frequency as counted from a smallest erythrocyte size in the erythrocyte size distribution diagram agrees with A % of the total erythrocytes, whereby the erythrocyte size Xch at that position is calculated. Then, a preset standard Qch of the erythrocyte size may be provided, whereby the erythrocytes may be determined to be of glomerular origin if $X < Q$; and to be of non-glomerular origin if $X \geq Q$, and the result of the determination is displayed on the display device.

Further, a first preset standard Q1ch and a second preset standard Q2ch may be provided ($Q1 < Q2$), whereby the erythrocytes may be determined to be of glomerular origin if $X < Q1$; to be of non-glomerular origin if $X \geq Q2$; and to be of a mixed kind that cannot be classified as any of the glomerular kind and the non-glomerular kind if $Q1 \leq X < Q2$.

To determine the type of erythrocytes in accordance with a distribution width value of a central region of the erythrocyte size distribution diagram is to monitor the distribution width value of the central region of the erythrocyte size distribution diagram for determining whether the erythrocytes in the urine are of single type or multiple type. This is for determining whether the erythrocytes in the urine are single-type erythrocytes of non-glomerular origin that have not been damaged or multiple-type erythrocytes that have been damaged.

The multiple-type erythrocytes that have been damaged include not only erythrocytes of glomerular origin such as bump-like erythrocytes and ring-like erythrocytes but also confetti-like erythrocytes and lysed erythrocytes created by change in osmotic pressure.

Specifically, as the width of the particle size distribution, a region containing B % of the total erythrocytes may be set in the middle of the particle size distribution diagram, and the width Ych of the region may be calculated. Further, a set width standard Wch may be used to determine that the erythrocytes are of single type if $Y < W$, and of multiple type if $Y \geq W$.

Also, the origin of erythrocytes maybe determined based on the distribution width value of the central region of the erythrocyte size distribution diagram.

Specifically, as the width of the particle size distribution diagram, a region containing B % of the total erythrocytes may be set in the middle of the particle size distribution diagram, and the width Ych of the region may be calculated. Further, set width standards Wch1 and Wch2 ($W1 < W2$) may be used to determine that the erythrocytes are of non-glomerular origin if $Y < W1$, of glomerular origin if $W1 \leq Y < W2$, and of mixed kind which cannot be classified as any of the glomerular and non-glomerular kinds if $W2 \leq Y$.

Further, by combining the erythrocyte size Xch and the distribution width Ych, the origin and type of the erythrocytes may be determined with improved precision on the basis of the information reflecting the morphology of the erythrocytes.

Specifically, the region represented by the inequality $Q2 \leq X$ may be divided into a region represented by $Y < W$ and a region represented by $W < Y$. The erythrocytes satisfying the inequalities $Q2 \leq X$ and $Y < W$ may be determined as single-type erythrocytes of non-glomerular origin which retain their morphology without being damaged so much. The erythrocytes satisfying the inequalities $Q2 \leq X$ and $W < Y$ can be determined as multiple-type erythrocytes, which are mixed-kind erythrocytes that cannot be classified as erythrocytes of non-glomerular origin because they include damaged erythrocytes in addition to erythrocytes of non-glomerular origin which retain their morphology without being damaged so much. This combination may be set in various ways in accordance with the needs.

EXAMPLES

Hereafter, the present invention will be explained in detail on the basis of the embodiments thereof with reference to the attached drawings. However, these embodiments are not intended to limit the scope of the present invention. Construction of the apparatus for differentiating erythrocytes FIG. 1 is a view illustrating a construction of an optical system in a flow cytometer which is an apparatus for differentiating erythrocytes in urine according to the present invention.

Figure 1:
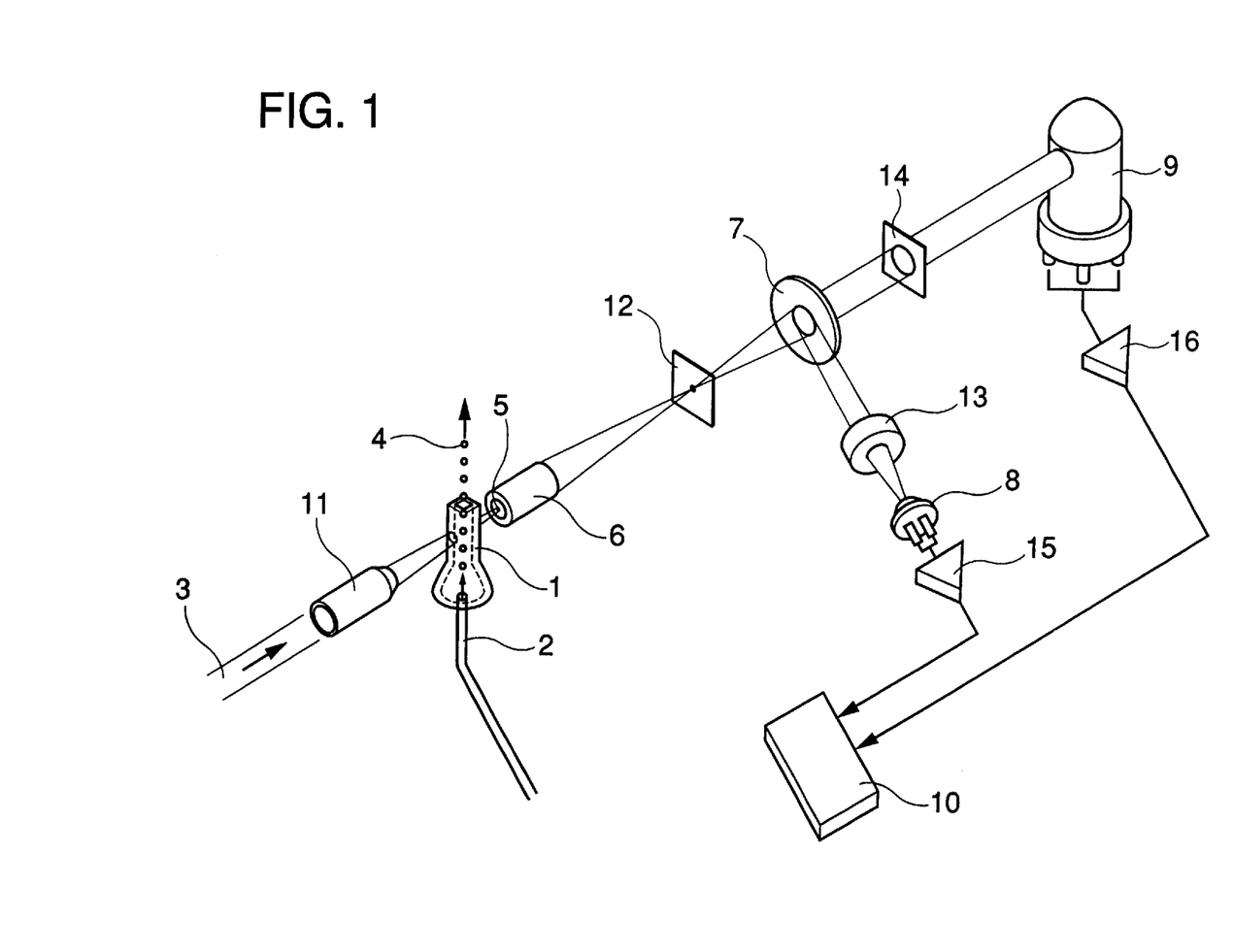
FIG. 1 is a view illustrating a construction of an optical system in an apparatus according to an embodiment of the present invention.

Referring to FIG. 1, a sheath flow cell 1 forms a urine specimen flow by allowing a urine specimen pretreated by a fluorescence staining process and injected from a sample nozzle 2 to be surrounded by a sheath liquid. An argon laser beam 3 irradiates a particle 4 in the urine specimen flow via a lens 11. The light which is transmitted directly through the urine specimen flow is stopped by a beam stopper 5. A forward scattered light and a forward fluorescent light released by the particle 4 are collected by a collector lens 6 to pass through a pinhole 12. Then, the forward scattered light is reflected by a dichroic filter 7 to pass through a lens 13 to be detected by a photodiode 8, whereas the forward fluorescent light is transmitted through the dichroic filter 7 to pass through a filter 14 to be detected by a photomultiplier tube 9. Signals detected by the photodiode 8 and the photomultiplier tube 9 are amplified by amplifiers 15, 16, respectively, to be input into a signal processing device 10.

Figure 2:
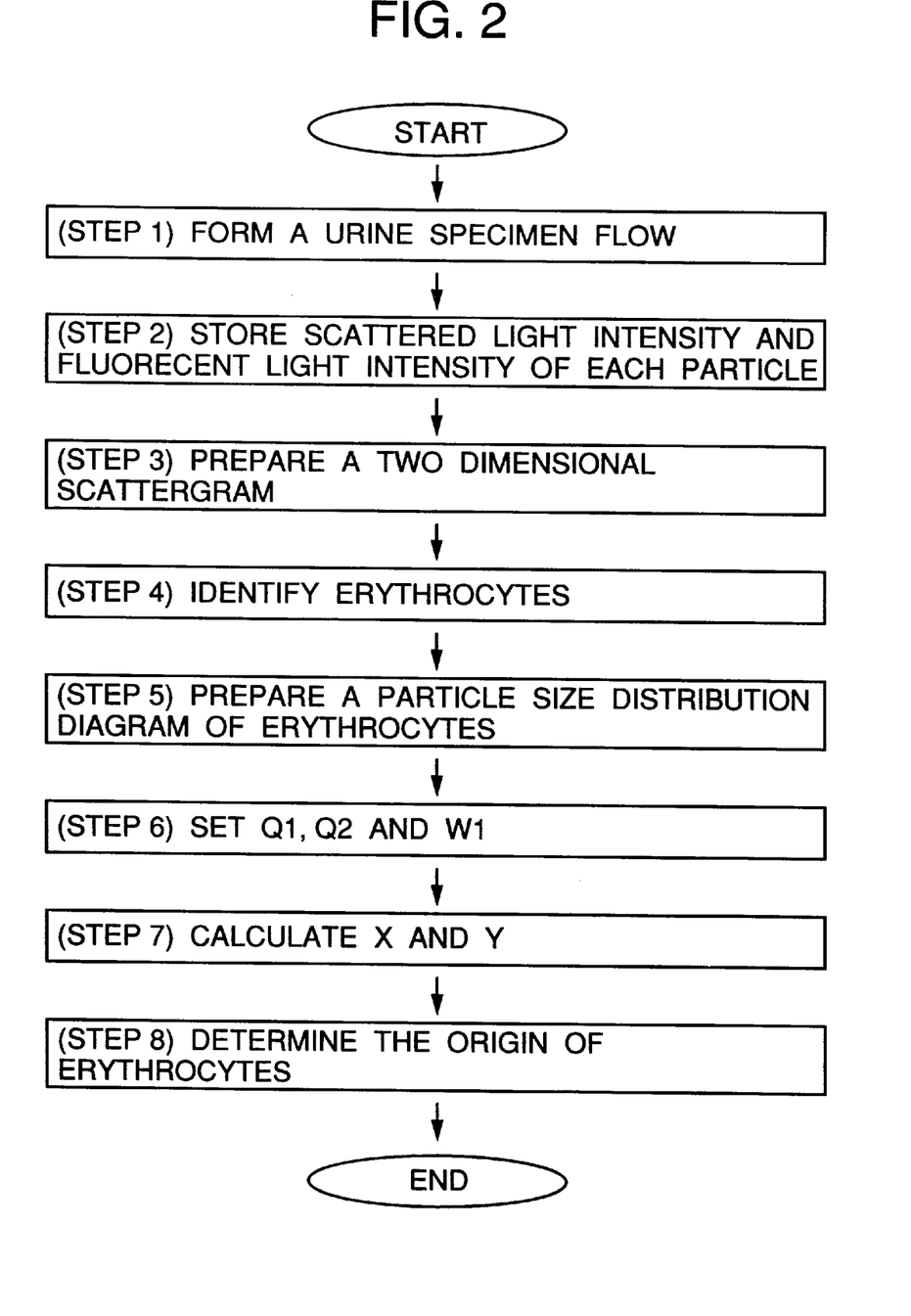
FIG. 2 is a flow chart illustrating basic operations of the apparatus according to the embodiment of the present invention.

Fundamental operations of the apparatus having such a construction will now be explained with reference to the flowchart shown in FIG. 2.

First, a urine specimen is prepared by diluting urine with a diluent and adding a staining solution. The urine specimen is then injected from the sample nozzle 2 into the sheath flow cell 1 together with a sheath liquid to form the urine specimen flow (step 1).

At the same time, an argon laser beam 3 is applied to the urine specimen flow. The forward scattered light and the forward fluorescent light emitted by each particle 4 are detected by the photodiode 8 and the photomultiplier tube 9, respectively. Intensities of the forward scattered light and the forward fluorescent light thus detected are stored in the signal processing device 10 (step 2).

Next, the signal processing device 10 prepares a two-dimensional scattergram with the intensities of the forward scattered light and the forward fluorescent light used as parameters and displays the scattergram on a display device (not shown) (step 3).

FIG. 3 shows an example of two-dimensional distribution diagram (scattergram) of the intensities of the "fluorescent and scattered lights" displayed on the display device of the present apparatus. FSC represents the intensity of the forward scattered light, which reflects the cross-sectional area of each cell. FL represents a stained intensity of the fluorescent light. In nucleus staining, it reflects the amount of DNA and RNA. In staining, membrane staining is also conducted because it is not possible to differentiate crystals, cells with no nuclei, and erythrocytes by nucleus staining alone. Thus, it is possible to distinctly classify the particles into erythrocytes, leukocytes, epithelial cells, bacteria, fungi, urinary casts, and crystal components in accordance with the size of the particle and the intensity of the fluorescent light, whereby each of the numbers thereof can be counted (step 4).

A particle size distribution diagram of the identified erythrocytes (in this case, a histogram with the intensity of the forward scattered light used as a parameter) is then prepared (step 5).

Then, with respect to the forward scattered light intensity, first and second standards Q1ch and Q2ch for the erythrocyte size and a third standard Wch for the erythrocyte size distribution width are set (step 6).

The erythrocyte size Xch at which an accumulated frequency of erythrocytes as counted from a smallest size in the particle size distribution diagram agrees with A % (50<A≦100) of the total erythrocytes is calculated. Further, a region containing B % of the total erythrocytes is set in the middle of the particle size distribution diagram, and the width Ych of the region is calculated (step 7).

Next, when the standards Q1ch, Q2ch, and Wch are set, the erythrocytes satisfying the inequality X<Q1 are determined to be of glomerular origin, those satisfying the inequality Q1≦X<Q2 to be of mixed kind (i.e. non-glomerular and glomerular), those satisfying the inequalities Q2≦X and Y<W to be of non-glomerular origin, and those satisfying the inequalities Q2≦X and W<Y to be of mixed kind (i.e. non-glomerular and glomerular). The judgment results are displayed on the display device (step 8).

As samples for differentiation, 66 urine specimens collected on the day of inspection (including those containing erythrocytes of glomerular origin, those containing erythrocytes of non-glomerular origin, and those containing erythrocytes of mixed kind) were measured by means of the above-mentioned apparatus in an inspection room of a hospital. The urine specimens had been collected on the day of measurement.

For contrasting the differentiation results, a laser microscope was used to determine the urine specimens containing 70% or more of deformed erythrocytes to be of glomerular origin, those containing 30% or more and less than 70% of deformed erythrocytes to be of mixed kind, and those containing less than 30% of deformed erythrocytes to be of non-glomerular origin.

First, the erythrocytes in these urine specimens were differentiated by the conventional method. As a differentiation condition, L1 and L2 were set to be 84ch and 126ch, respectively, which are set values given in the Examples of the Japanese Unexamined Patent Publication No. Hei 8(1996) -240520. Using this condition, those satisfying the inequality Ra2/Raz≧0.8 were determined to be of glomerular origin, those satisfying the inequality Ra1/Raz≧0.8 to be of non-glomerular origin, those satisfying none of the above two inequalities to be of mixed kind, and those satisfying both of the above two inequalities to be of non-glomerular origin. The results are shown in Table 2.

Out of the 34 urine specimens that were determined to be of non-glomerular origin by microscopy, 14 urine specimens were incorrectly identified as being of glomerular origin by the conventional method.

TABLE 2

| Judgment by prior art method | Judgment by microscopy | | | |
| --- | --- | --- | --- | --- |
| | non-glomerular origin | mixed kind | glomerular origin | Total |
| non-glomerular origin | 18 | 1 | 0 | 19 |
| mixed kind | 2 | 0 | 1 | 3 |
| glomerular origin | 14 | 12 | 18 | 44 |
| Total | 34 | 13 | 19 | 66 |

Example 1

In order to reflect the presence of non-glomerular-origin erythrocytes that retain their original shape, the particle size distribution value is set at a position where an accumulated frequency of erythrocytes as counted from a smallest size in the particle size distribution diagram agrees with A % (50<A≦100) of the total erythrocytes. If the value A is near 50%, it is approximately equal to the median of the particle size distribution diagram, so that the value is liable to be affected by the damaged erythrocytes. On the other hand, if the value A is near 100%, it is affected by the presence of an extremely small amount of non-glomerular-origin erythrocytes, thereby providing poor accuracy. Therefore, the value A is preferably within the range of 60 to 90%.

Figure 4:
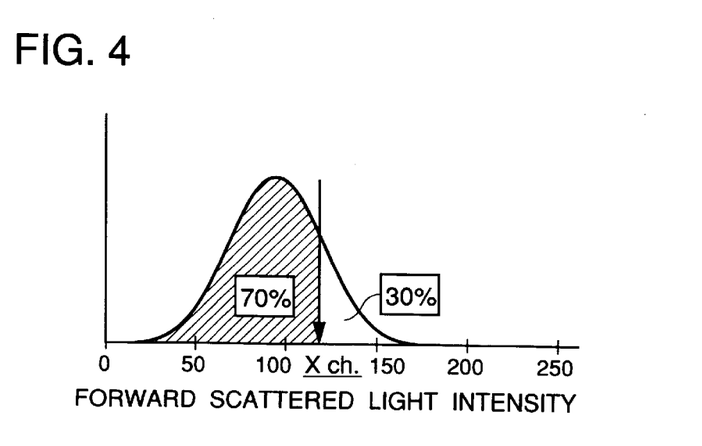
FIG. 4 is a view for explaining a size X of erythrocytes as a determining parameter according to the embodiment of the present invention.

FIG. 4 shows the erythrocyte size Xch as the particle size distribution value when the value A is set to be 70%.

Table 3 shows judgment results when the first standard Q1 for determining the glomerular origin is set to be 80ch, the second standard Q2 for determining the non-glomerular origin is set to be 100ch, and the erythrocytes falling between the first and second standards Q1 and Q2 are determined to be of mixed kind.

In the conventional method, 14 specimens out of the 34 non-glomerular-origin specimens were mistakenly identified as being of glomerular origin. According to the judgment of this Example, only 4 specimens were mistakenly identified as being of glomerular origin, thereby showing a great improvement in accuracy.

TABLE 3

| Judgment by Example 1 | Judgment by microscopy | | | |
| --- | --- | --- | --- | --- |
| | non-glomerular origin | mixed kind | glomerular origin | Total |
| non-glomerular origin | 22 | 2 | 1 | 25 |
| mixed kind | 8 | 3 | 1 | 12 |
| glomerular origin | 4 | 8 | 17 | 29 |
| Total | 34 | 13 | 19 | 66 |

Figure 5:
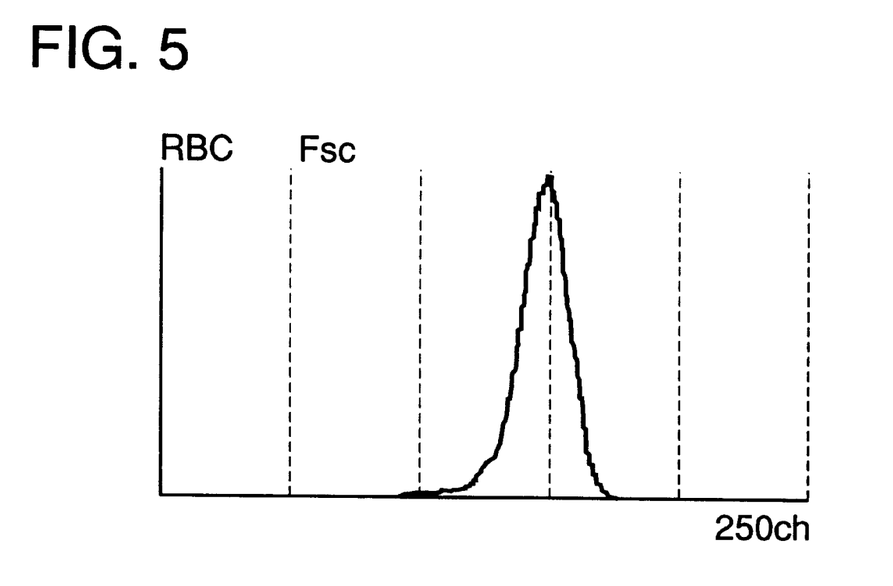
FIG. 5 is a view showing an example of an erythrocyte size distribution diagram obtained by the apparatus according to the embodiment of the present invention.

FIG. 5 shows a typical particle size distribution diagram of non-glomerular-origin erythrocytes according to an analysis by the apparatus of the present invention. In this specimen, non-glomerular-origin erythrocytes have not been damaged in urine, so that the median of the distribution diagram is shifted to a larger size, and the particle size distribution width is small. Since the particle size distribution of this specimen is shifted to a larger size, the conventional method gives correct identification of the specimen as being of non-glomerular origin, because Ra2/Raz=0.07 and Ra1/Raz=0.99. The method of the present invention also gives correct identification of the specimen as being of non-glomerular origin, because X=148ch.

Figure 6:
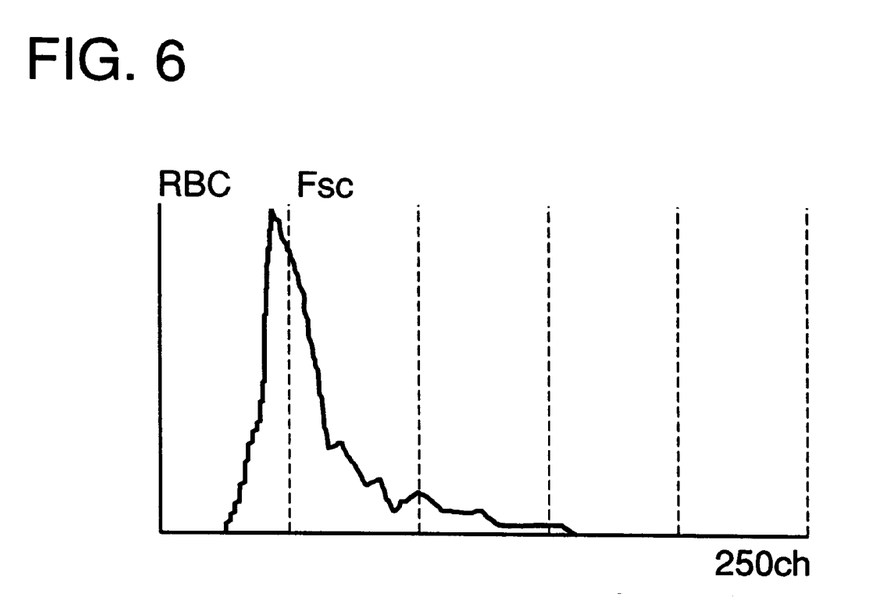
FIG. 6 is a view showing an example of an erythrocyte size distribution diagram obtained by the apparatus according to the embodiment of the present invention.

FIG. 6 shows a typical particle size distribution diagram of glomerular-origin erythrocytes according to an analysis by the apparatus of the present invention. In this specimen, the median of the distribution diagram is shifted to a smaller size, and the particle size distribution width is large. Since the particle size distribution of this specimen is shifted to a smaller size, the conventional method gives correct identification of the specimen as being of glomerular origin, because Ra2/Raz=0.97 and Ra1/Raz=0.14. The method of the present invention also gives correct identification of the specimen as being of glomerular origin, because X=61ch.

Figure 7:
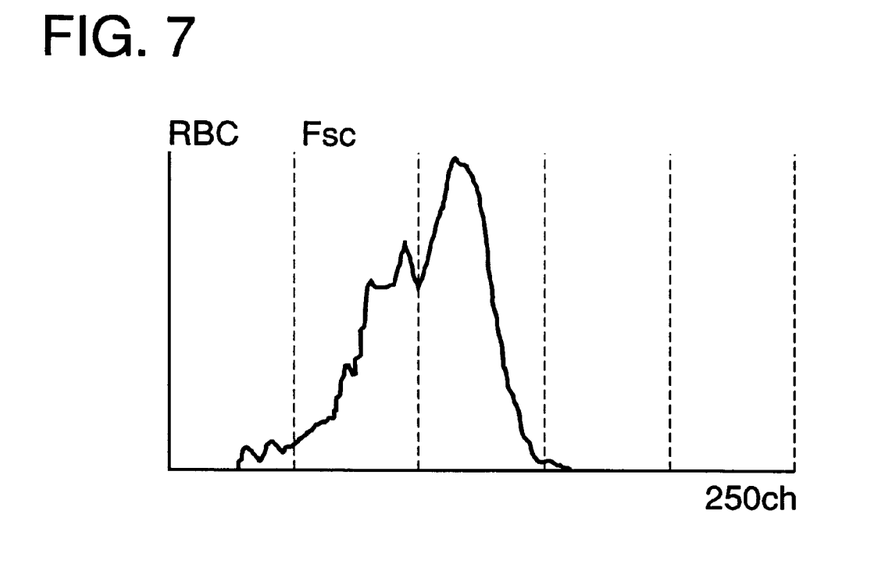
FIG. 7 is a view showing an example of an erythrocyte size distribution diagram obtained by the apparatus according to the embodiment of the present invention.

FIG. 7 shows an example of a particle size distribution diagram of non-glomerular-origin erythrocytes that have been damaged in urine, according to an analysis by the apparatus of the present invention. In this specimen, the overall particle size distribution is shifted to a smaller size.

Since the particle size distribution of this specimen is shifted to a smaller size, the conventional method gives mistaken identification of the erythrocytes as being of glomerular origin, because Ra2/Raz=0.92 and Ra1/Raz=0.70. However, since the specimen still contains erythrocytes that retain their morphology to some extent, the method of the present invention gives correct identification of the erythrocytes as being of non-glomerular origin, because X=113ch.

Figure 8:
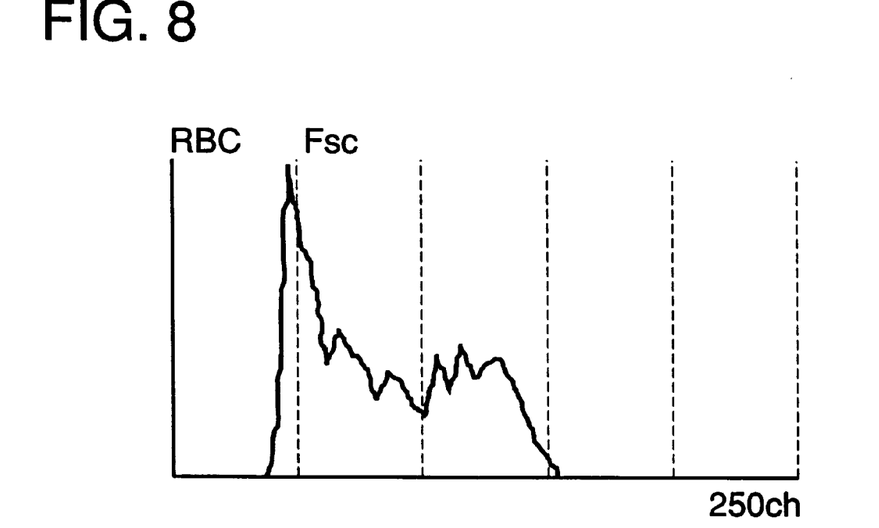
FIG. 8 is a view showing an example of an erythrocyte size distribution diagram obtained by the apparatus according to the embodiment of the present invention.

FIG. 8 shows another example of a particle size distribution diagram of non-glomerular-origin erythrocytes that have been damaged in urine, according to an analysis by the apparatus of the present invention. In this specimen, two peaks appear in the particle size distribution diagram because the degree of damage varies depending on each erythrocyte. Since the particle size distribution of this specimen is shifted to a smaller size, the conventional method gives mistaken identification of the erythrocytes as being of glomerular origin, because Ra2/Raz=0.89 and Ra1/Raz=0.44. However, since the specimen still contains erythrocytes that retain their morphology to some extent, the method of the present invention gives correct identification of the erythrocytes as being of non-glomerular origin, because X=103ch.

Example 2

Figure 9:
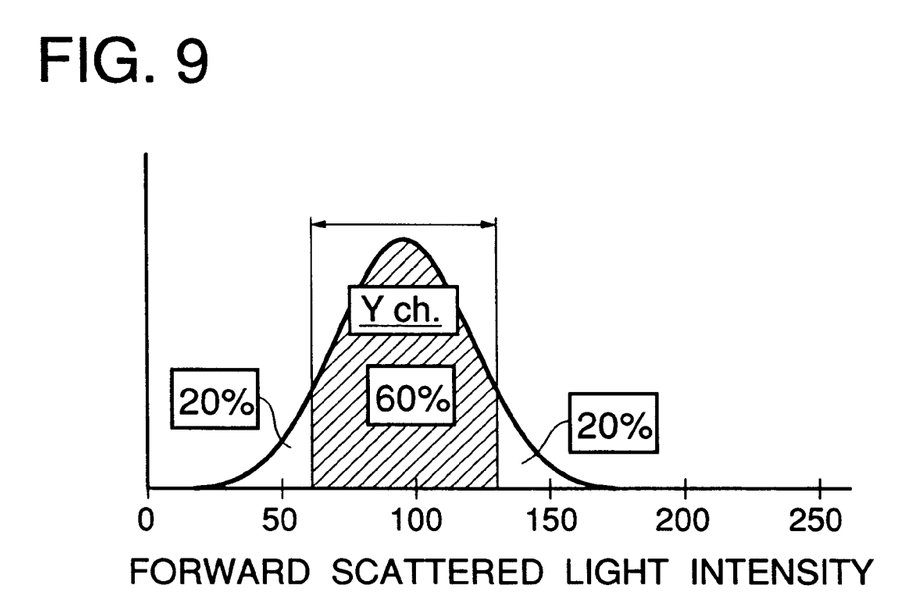
FIG. 9 is a view for explaining a width Y of the erythrocyte size distribution diagram as another determining parameter according to the embodiment of the present invention.

In order to determine the type of erythrocytes, a region occupying B % of the total erythrocytes was set in the middle of the particle size distribution diagram as a width data of the erythrocyte size distribution diagram. The distribution width Y of the region was used for determination of the type of erythrocytes. In order to reflect the overall particle size distribution, the value of B is preferably within the range of 50 to 90%. FIG. 9 shows the erythrocyte distribution width Ych as the particle size distribution value when the value B is set to be 60%.

Table 4 shows judgment results when the standard W for determining the type of erythrocytes is set to be 40ch so as to determine the erythrocytes satisfying the inequality $Y \geq 40$ to be of multiple type and the erythrocytes satisfying the inequality $Y < 40$ to be of single type.

This judgment makes it possible to determine whether the erythrocytes are of single type that can be classified into either glomerular-origin erythrocytes or non-glomerular-origin erythrocytes, or of mixed kind that cannot be classified into any of the above-mentioned two kinds (glomerular and non-glomerular).

Some specimens of non-glomerular origin are determined to be of multiple type because the erythrocytes have been damaged to lose their original morphology, though they are erythrocytes of non-glomerular origin.

TABLE 4

| Judgment by Example 2 | Judgment by microscopy | | | |
| --- | --- | --- | --- | --- |
| | non-glomerular origin | mixed kind | glomerular origin | Total |
| multiple type | 15 | 11 | 3 | 18 |
| single type | 19 | 2 | 16 | 29 |
| Total | 34 | 13 | 19 | 66 |

Example 3

Figure 10:
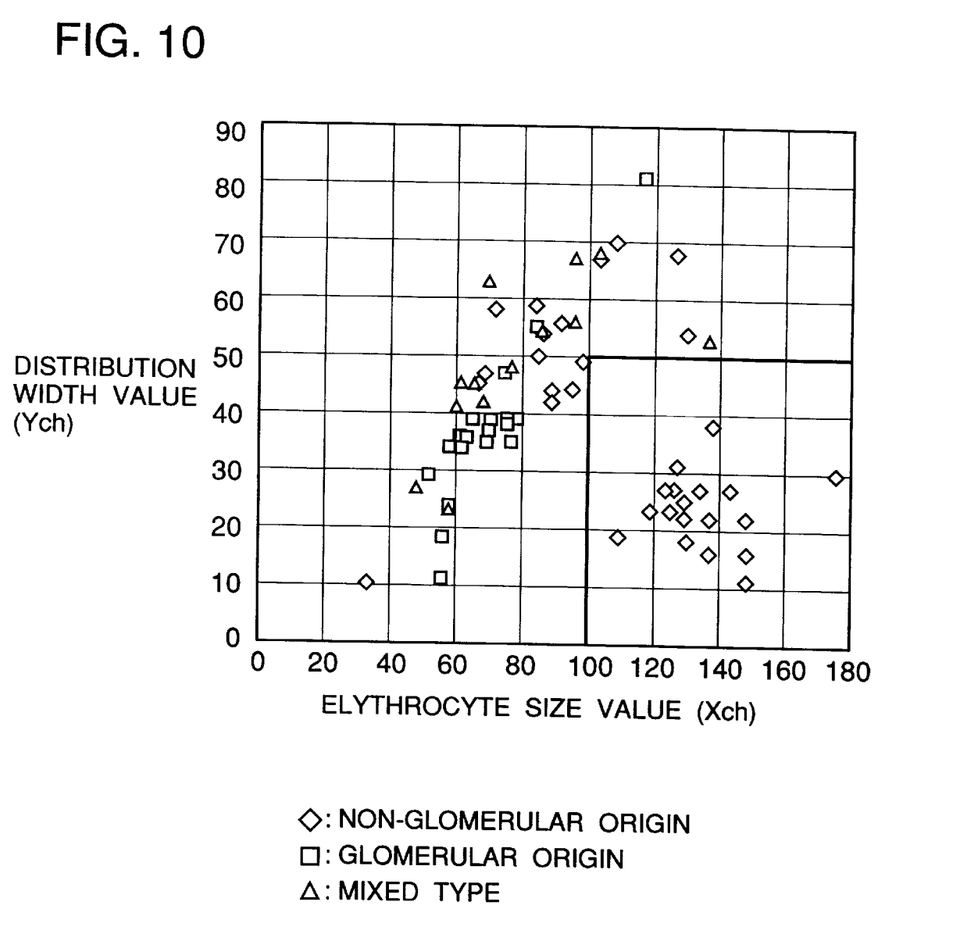
FIG. 10 is a graph obtained by plotting the size X of erythrocytes and the width Y of the erythrocyte size distribution diagram as determining parameters according to the embodiment of the present invention.

Further, by combining the width Y and the size X of the particle size distribution, it is possible to conduct a more accurate determination of the origin and type of erythrocytes based on a data that reflects the morphology of the erythrocytes. FIG. 10 is a graph obtained by plotting the size Xch of the erythrocytes in Example 1 and the width Ych of the erythrocyte size distribution.

Specifically, by using the erythrocyte size distribution width Ych, the non-glomerular-origin region in which the erythrocyte size Xch satisfies the inequality $X \geq 100ch$ can be divided into a region represented by $Y < 50ch$ and a region represented by $Y \geq 50ch$. The erythrocytes satisfying the inequalities $X \geq 100ch$ and $Y < 50ch$ can be determined as single-type erythrocytes of non-glomerular origin which retain their morphology without being damaged so much. The erythrocytes satisfying the inequalities X≧100ch and Y≧50ch can be determined as multiple-type erythrocytes, which are mixed-kind erythrocytes that include damaged erythrocytes. Here, the specimen shown in FIG. 8 is determined to be of multiple type, which is a mixed kind, because the erythrocyte size distribution width is Y=68ch. The results of the judgment thus carried out are shown in Table 5.

TABLE 5

| Judgment by Example 3 | Judgment by microscopy | | | |
| --- | --- | --- | --- | --- |
| | non-glomerular origin | mixed kind | glomerular origin | Total |
| non-glomerular origin | 18 | 0 | 0 | 18 |
| mixed kind | 12 | 5 | 2 | 19 |
| glomerular origin | 4 | 8 | 17 | 29 |
| Total | 34 | 13 | 19 | 66 |

For clinical application, an efficient and accurate inspection can be conducted by examining the morphology of the erythrocytes by means of a laser microscope based on the data obtained by determining the specimens appearing in the region satisfying X≧Q2 and Y<W to be non-glomerular-origin erythrocytes that retain their morphology and by determining the specimens appearing in the other regions to be erythrocytes that do not retain their morphology.

Example 4

Also, by observing the relationship between the distribution width Y and the origin of erythrocytes, it is understood that the origin of erythrocytes can be determined by means of the distribution width Y alone. On further inspection of the specimens determined to be of single type, the erythrocytes of non-glomerular origin exhibit a smaller distribution width Y than the erythrocytes of glomerular origin. Specifically, as standards for determining the origin of erythrocytes, the first standard W1 may be set to be 40ch and the second standard W2 to be 32cn to determine the region Y≧W1 to be of mixed kind, the region W1>Y≧W2 to be of glomerular origin, and the region W2>Y to be of non-glomerular origin. The results are shown in Table 6.

TABLE 6

| Judgment by Example 4 | Judgment by microscopy | | | |
| --- | --- | --- | --- | --- |
| | non-glomerular origin | mixed kind | glomerular origin | Total |
| non-glomerular origin | 15 | 2 | 4 | 21 |
| mixed kind | 15 | 11 | 3 | 29 |
| glomerular origin | 4 | 0 | 12 | 16 |
| Total | 34 | 13 | 19 | 66 |

Here, the determination standards in microscopy are not yet unified, and there are many ratios of deformed erythrocytes that can be used as a standard for determination of their origin. Therefore, the determining values may be changed in accordance with the intended sensitivity in the determining process.

The present invention makes it possible to determine the origin and type of erythrocytes in urine with high accuracy by monitoring the morphology of the erythrocytes even if the erythrocytes are damaged by aciduria, hyposthenuria, or the like.

Although the present invention has fully been described byway of example with reference to the accompanying drawings, it is to be understood that various changes and modifications will be apparent to those skilled in the art. Therefore, unless such changes and modifications depart from the scope of the invention, they should be construed as being included therein.

What we claim is:

1. An apparatus for differentiating erythrocytes in urine, comprising:

a light source for applying light to a urine specimen flow;

a light sensor for detecting light emitted by particles in the urine specimen flow;

identification means for identifying erythrocytes in the urine specimen flow in accordance with detected light;

a processor for determining an origin of the erythrocytes based on a particle size distribution of the identified erythrocytes by comparing an erythrocyte size value, X, at an $A^{th}$ percentile of the particle size distribution for identified erythrocytes with a reference value, A being greater than 50; and an output for outputting a determination result.

2. The apparatus of claim 1, wherein said processor further determines an origin and type of the identified erythrocytes in accordance with X and a distribution width value, Y, of a central region of the particle size distribution, the central region being defined as a percentage of the total number of identified erythrocytes.

3. The apparatus of claim 2, wherein said processor determines that the identified erythrocytes are of non-glomerular origin or of glomerular origin based on the values of X and Y.

4. The apparatus of claim 2, wherein said processor determines that the identified erythrocytes are of mixed glomerular and non-glomerular origin based on the values of X and Y.

5. The apparatus of claim 1, wherein A is within the range of 60 to 90.

6. The apparatus of claim 1, further comprising:

a sheath flow cell for forming the urine specimen flow by surrounding a urine specimen with a sheath liquid.

7. The apparatus of claim 1, wherein said processor determines that the identified erythrocytes are of non-glomerular origin when X is greater than or equal to a first reference value, and determines that the identified erythrocytes are of glomerular origin when X is less than a second reference value.

8. The apparatus of claim 7, wherein said processor determines that the identified erythrocytes are of mixed glomerular and non-glomerular origin when X is less than the first reference value and greater than or equal to the second reference value.

9. The apparatus of claim 1, wherein said processor compares the erythrocyte size value at the $A^{th}$ percentile to discriminate damaged non-glomerular origin erythrocytes from glomerular origin erythrocytes.

10. An apparatus for differentiating erythrocytes in urine, comprising:

a light application source for applying light to a urine specimen flow;

a light sensor for detecting light emitted by particles in the urine specimen flow;

identification means for identifying erythrocytes in the urine specimen flow in accordance with detected light; and a processor for determining a type of the identified erythrocytes based on a distribution width value, Y, of a central region in a particle size distribution, the central region being defined by a preset percentage of the total identified erythrocytes.

11. The apparatus of claim 10, wherein said processor further determines an origin of the erythrocytes in accordance with the distribution width value.

12. The apparatus of claim 10, wherein the preset percentage is within the range of 50% to 90%.

13. The apparatus of claim 10, further comprising:

a sheath flow cell for forming the urine specimen flow by surrounding a urine specimen with a sheath liquid.

14. The apparatus of claim 10, wherein said processor determines that the identified erythrocytes are of a single type that can be classified into either glomerular origin erythrocytes or non-glomerular origin erythrocytes when Y is less than a first reference value.

15. The apparatus of claim 14, wherein said processor determines that the identified erythrocytes are of a mixed type that cannot be classified into one of glomerular origin erythrocytes and non-glomerular origin erythrocytes when Y is greater than or equal to the first reference value.

16. A method for differentiating erythrocytes in urine, comprising the steps of:

applying light to a urine specimen flow;

detecting light emitted by particles in the urine specimen flow;

identifying erythrocytes from the particles in the urine specimen flow in accordance with the detected light; and determining an origin of the identified erythrocytes based on a particle size distribution of the identified erythrocytes by comparing an erythrocyte size value, X, at an $A^{th}$ percentile of the particle size distribution for identified erythrocytes with a reference value, A being greater than 50.

17. The method of claim 16, wherein said determining step further determines an origin and type of the identified erythrocytes in accordance with X and a distribution width value, Y, of a central region of the particle size distribution, the central region being defined as a percentage of the total number of identified erythrocytes.

18. The method of claim 16, wherein A is within the range of 60 to 90.

19. The method of claim 16, further comprising:

forming the urine specimen flow using a sheath flow cell.

20. The method of claim 16, wherein said step of determining determines that the identified erythrocytes are of mixed glomerular and non-glomerular origin when X is less than the first reference value and greater than or equal to the second reference value.

21. The method of claim 20, wherein said step of determining compares the erythrocyte size value at the $A^{th}$ percentile to discriminate damaged non-glomerular origin erythrocytes from glomerular origin erythrocytes.

22. The method of claim 16, wherein said determining step further determines that the identified erythrocytes are of non-glomerular origin or of glomerular origin based on the values of X and Y.

23. The method of claim 16, wherein said determining step further determines that the identified erythrocytes are of mixed glomerular and non-glomerular origin based on the values of X and Y.

24. A method for differentiating erythrocytes in urine, comprising the steps of:

applying light to a urine specimen flow;

detecting light emitted by particles in the urine specimen flow;

identifying erythrocytes from the particles in the urine specimen flow in accordance with the detected light; and determining a type of the identified erythrocytes based on a distribution width value, Y, of a central region in a particle size distribution, the central region being defined by a preset percentage of the total identified erythrocytes.

25. The method of claim 24, wherein the determining step further determines an origin of the identified erythrocytes in accordance with the distribution width value.

26. The method of claim 24, wherein the preset percentage is within the range of 50% to 90%.

27. The method of claim 24, further comprising:

forming the urine specimen flow using a sheath flow cell.

28. The method of claim 24, wherein said determining step determines that the identified erythrocytes are of a single type that can be classified into either glomerular origin erythrocytes or non-glomerular origin erythrocytes when Y is less than a first reference value.

29. The method of claim 28, wherein said determining step determines that the identified erythrocytes are of a mixed type that cannot be classified into one of glomerular origin erythrocytes and non-glomerular erythrocytes when Y is greater than or equal to the first reference value.

* * * * *